United States Patent [19]

Pruett

[11] Patent Number: 4,673,399
[45] Date of Patent: Jun. 16, 1987

[54] DISPOSABLE INJECTION TRANSMITTER

[75] Inventor: Earl M. Pruett, St. Louis, Mo.

[73] Assignee: Enrico Bertucci, Belleville, Ill. ; a part interest

[21] Appl. No.: 741,842

[22] Filed: Jun. 6, 1985

[51] Int. Cl.⁴ ........................ A61M 5/16; A61M 27/00
[52] U.S. Cl. ..................................... 604/272; 604/411; 604/86
[58] Field of Search .................. 604/272, 86, 88, 148, 604/205, 201, 244, 411, 415

[56] References Cited

U.S. PATENT DOCUMENTS

| | | | |
|---|---|---|---|
| 2,587,784 | 3/1952 | Story, Jr. ............................. | 604/86 |
| 3,098,481 | 7/1963 | Wikander et al. .................. | 604/411 |
| 4,133,441 | 1/1979 | Mittleman ......................... | 604/86 X |
| 4,219,912 | 9/1980 | Adams ................................. | 604/86 |
| 4,505,709 | 3/1985 | Froning et al. ..................... | 604/411 |
| 4,507,113 | 3/1985 | Dunlap ............................... | 604/411 |
| 4,543,101 | 9/1985 | Crouch ............................. | 604/86 X |

FOREIGN PATENT DOCUMENTS 1054174 10/1953 France .................................. 604/86

Primary Examiner—Stephen C. Pellegrino
Attorney, Agent, or Firm—Rogers, Howell, Moore & Haferkamp

[57] ABSTRACT

A disposable injection transmitter for use between injecting needles and a primary injection site. A body having a passage through it. A hollow auxiliary needle joined to the body in communication with one end of the passage and adapted to penetrate through and reside in the primary injection site. An elastomeric wall joined to the body and covering the other end of the passage and adapted to receive a series of injecting needles through it to inject fluids into or beyond the passage.

16 Claims, 8 Drawing Figures

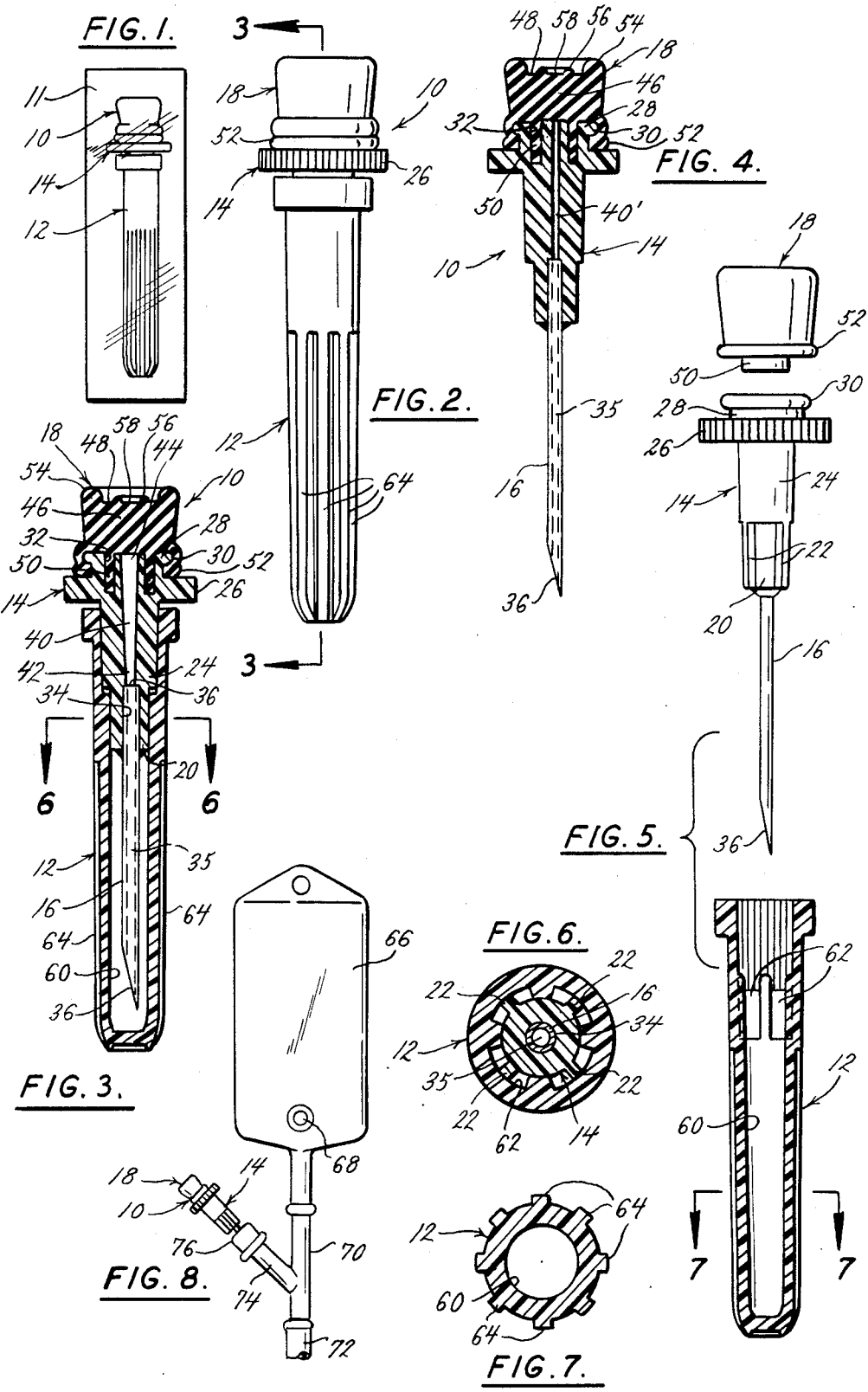

DISPOSABLE INJECTION TRANSMITTER

BACKGROUND OF THE INVENTION

This invention relates to a disposable injection transmitter having a needle for piercing and residing at a primary injection site and having an auxiliary injection site for receiving a plurality of fluid injections, thereby reducing the number of punctures of the primary injection site.

As is known in the health care field, injections are frequently made by sticking a needle through a wall or membrane of what is known as an injection site and introducing fluid through the needle. These injection sites are provided on various medical devices. Typically the injection site is made of an elastomeric material, such as latex, that is attached to the medical device. For example, a typical IV fluid container, such as a bag, has an injection site on a side wall of the bag or at the end of a short tube leading to the bag, or an IV bottle has an injection site in its upper wall. The injection site, in the form of a wall or membrane, can be penetrated by a needle to allow an injection to be forced into the bag. Depending upon a particular patient's prescription, several separate injections may be made into the bag. In fact, it is typical that more than one injection is made before the bag is put into use.

Once the bag has been filled and the injections have been made, the bag may have a replacement value of three to four hundred dollars. Of course, it is vitally important that the contents of the bag remain sterile. To maintain sterility, the bag must not be exposed to unfiltered atmospheric air. An advantage of the plastic IV bag is that is collapses as it is emptied, as distinguished from a glass bottle which is not collapsible and therefore requires the introduction of filtered air into the area above the fluid level as the bottle is emptied.

It is estimated that before an IV bag is put to use, an average of about three injections are introduced into an IV bag, and sometimes many more, before the bag is used. These injections will range from low to high viscosity fluids injected with small to large needles.

The recurring problem with the elastomeric injection site on the IV bag is that injections can damage it. This damage can occur in the form of leakage through a hole in the injection site made large by multiple needle sticks at the same spot, or leakage caused by coring. Coring occurs when part of the injection site is actually cut or torn away. The coring can be total, in which case a piece of the elastomeric material is separated from the injection site, enters the bag, and leaves a hole in the membrane; or partial in which case a piece of the membrane breaks away but remains attached to the injection site, nevertheless leaving a hole that allows leakage.

As soon as leakage occurs, the contents of the bag are exposed to the atmosphere and to potential contamination, and must be discarded. When coring occurs, there is the additional contamination from a piece of the injection site membrane entering the bag. In either case, the protection of the patient requires that the bag and its contents be discarded. Each time this happens, it can result in a loss of three to four hundred dollars.

Another problem that occur is the introduction of an injecting needle through a side of the injection site by a careless health practitioner or one who is in a hurry. This likewise can cause leakage and loss of the contents of the bag, because it must be discarded.

Another example of a common use of an injection site is on a tributary to a tube that is transmitting fluids to a patient (such as to a vein). In this use of an injection site, it is common that there be periodic times when a plurality of injections are made in the injection site. At each of these times, a plurality of injections are made to introduce a plurality of different medicines into the tube to be conveyed with the fluid as prescribed for a particular patient. In this practice, the problems of creating an open hole because of frequent introduction of needles at the same spot, or of coring, are compounded. Again, any air leakage means the primary source of the fluid, such as an IV bag, must be discarded. Furthermore, the leakage introduces atmospheric contamination directly into the tube and directly into the patient and can be extremely hazardous to the patient's health.

A third example of an injection site that receives multiple injections is sometimes referred to as an "infuse-aid". The infuse-aid is a rubber or elastomeric membrane planted under a patient's skin, usually in a large artery or vein. The infuse-aid is used for patients who have poor veins or other reasons they cannot receive multiple injections, such as a leukemia patient. The infuse-aid implant is very expensive. The membrane costs about $400 and it must be implanted in a hospital, which is costly. The infuse-aid is used for introducing multiple injections on a periodic basis into the patient's vein.

An infuse-aid presents the aforesaid risks of developing a hole that leaks to atmosphere or of coring, either of which can produce immediate contamination to the patient. Since the life of an infuse-aid allows a limited number of injections sticks, generally about 200, it must be replaced on a recurring basis, which is repetitively costly.

The present invention virtually eliminates the problem of contamination of the IV bag and eliminates or greatly reduces the prospects of leakage or coring that has heretofore occurred at injection sites.

SUMMARY OF THE INVENTION

This invention comprises a disposable injection transmitter having a body with an auxiliary needle extending from one end of the body and an auxiliary injection site in the form of an elastomeric wall or membrane at the other end of the body. There is a passage through the body between the auxiliary needle and the auxiliary injection site.

An injection needle stuck through the auxiliary injection site membrane introduces injected fluid into the passage in the body, or alternatively, the injecting needle extends through the membrane and through the body passage into the auxiliary needle. Since the auxiliary needle of the disposable injection transmitter has been introduced through the membrane of a conventional primary injection site, these injections are transmitted through that primary injection site. However, the auxiliary injection site, rather than the primary injection site, receives the multiple injections. After multiple injections have been made, the disposable injection transmitter is removed and discarded (its cost is extremely low), and a new one used for the next group of injections.

BRIEF DESCRIPTION OF THE DRAWINGS

FIG. 1 is a side elevation view of the disposable injection transmitter shown packaged in a sterile package;

FIG. 2 is an enlarged side elevation view of the disposable injection transmitter and its sheath;

FIG. 3 is a view in section along the plane of the line 3—3 of FIG. 2;

FIG. 4 is a view in section of the disposable injection transmitter similar to that of FIG. 3, but showing a modified form of the passage through the body;

FIG. 5 is an exploded side elevation view of the disposable injection transmitter and showing the sheath in longitudinal medial section;

FIG. 6 is a view in section on an enlarged scale taken along the plane of the line 6—6 of FIG. 3;

FIG. 7 is a view in section on an enlarged scale taken along the plane of the line 7—7 of FIG. 5; and FIG. 8 is a partial side elevation view on a reduced scale illustrating an IV bag with a fluid tube connected to it, and illustrating an injection site on the IV bag as well as an injection site on a tributary to the fluid tube, and further illustrating use of the disposable injection transmitter on the tributary injection site.

DETAILED DESCRIPTION OF THE PREFERRED EMBODIMENTS

Referring to the drawings, FIG. 1 shows the disposable injection transmitter 10 supplied within an air-tight clear plastic package 11 of conventional construction. The package 11 is torn away to gain access to the disposable injection transmitter 10. Part of the disposable injection transmitter is covered by a stiff plastic sheath 12.

Referring to FIG. 3, the injection system 10 comprises a body 14, an auxiliary needle 16 joined to one end of the body 14, and an auxiliary injection site 18 joined to the other end of the body 14. Preferably, the body 14 is formed of rigid and inexpensive plastic. The body 14 has a leading end 20 having longitudinal splines 22 adjacent to it followed by a larger body section 24 that is cylindrical and preferably leads to a radially outwardly extending wall 26. Although the wall 26 can be omitted, it offers advantages in insertion and removal of the needle 16 as will appear. The body 14 also has a trailing end 28 with an annular outwardly projecting rim 30 adjacent to it. There also may be an annular groove 32 in the face of the trailing end 28.

At the lead end 20 of the body 14, a recess 34 tightly and fixedly receives the auxiliary injection needle 16. The needle 16 is hollow as defined by a passage 35 through it from its lead end 36 to its trailing end 38.

There is a passage 40 through the body 14 leading from the recess 34 to the face of the trailing end 28. The passage 40 may be diverging as shown in FIG. 3 from its lead end 42 to its trailing end 44. The passage 40 is coaxial with the passage 34 through the needle 16 and preferably its lead end 42 is of substantially the same diameter as the diameter of the passage 35.

Alternatively, as shown in FIG. 4, the body 14 may be formed with a passage 40' that is of constant diameter. The diameter of the passage 40' is preferably the same as the diameter of the passage 35 through the needle 16. In either embodiment, it is preferable that the net volume within the passage 40 or 40' be minimized so that essentially all fluid injection will pass through the primary injection site. Therefore, the passage 35 is sized to receive most injecting needles, and the diameters of the passages 40 or 40' are minimized while still admitting a variety of injection needle diameters. Also, the length of either body passage 40 or 40' is only about ⅝ inch.

The auxiliary injection site 18 is formed with a wall or membrane 46 extending between the trailing end 28 of the body 14 and an outer face 48. This wall 48 is relatively thick, preferably between 2 and 5 mm., to reduce the possibility of coring and yet not so thick as to remove the silicone from an injection needle. The auxiliary injection site 18 may have a tubular extension 50 that cooperatively fits within the annular groove 32 in the body 14. There is also a resilient skirt 52 extending from the wall 46 of the auxiliary injection site 18 and fitting snugly around the annular rim 30.

The face 48 of the auxiliary injection site 18 is recessed within an outer annular rim 54. Spaced centrally therewithin is an outwardly projecting ring 56 that defines an injection area 58 within it.

The disposable injection transmitter 10 is furnished with a rigid plastic sheath 12 to protect the needle 16. The sheath 12 has an internal cavity 60. Adjacent the mouth of the cavity 60, there are a plurality of grooves 62 that cooperate with the splines 22 (see FIGS. 6 and 7) to provide a press-fit of the sheath 12 onto the body 14. The sheath 12 has longitudinal splines 64 on its outer wall to facilitate gripping for pulling the sheath 12 loose from the body 14.

FIG. 8 illustrates the use of this disposable injection transmitter 10. In FIG. 8, a typical IV fluid bag 66 is designed to hold fluid. An elastomeric injection site 68 (a primary or existing injection site) is provided on a lower side wall of the bag 66. Alternatively, the injection site 68 can be at the end of a short tube leading to the bag 66. In either case, the primary injection site 68 has a relatively thin elastomeric wall or membrane through which needles can be stuck for injecting various prescribed fluids into the bag 66. The bag 66 is shown connected to a Y juncture 70 leading to a tube 72 that in turn leads to the patient. Typically, the bag 66 will have the various additives injected through the injection site 68 before the bag is hooked up for use.

Therefore, if multiple injections through the injection site 68 produce a leaking hole or coring, the bag 66 will have to be discarded before it is ever used. Pursuant to the present invention, the needle 16 of the injection system 10 would be stuck through the primary injection site 68. This is facilitated if the radial wall 26 is included because manual pressure on the wall 26 will facilitate introduction and removal of the needle 16. Then the prescribed drugs or medicines would be added by sticking the secondary or auxiliary injection site 18 with the injecting needles. In this way, the primary injection site 68 is not subjected to multiple injections because only the single needle 16 penetrates it. After all the injections have been introduced to the bag 66, the disposable injection transmitter 10 is removed and discarded and the bag 66 is put to use.

FIG. 8 also illustrates a tributary tube 74 having a primary elastomeric injection site 76 on it. Conventionally, multiple injections are made in the primary injection site 66 on a periodic basis. These repetitions of multiple injections have caused the problems heretofore discussed of creating a leakage opening or closing.

As illustrated in FIG. 8, the disposable injection transmitter 10 is stuck in the primary injection site 76. Then a group of injections are made into the auxiliary injection site 18. Following this, the disposable injection transmitter 10 is withdrawn and discarded. The next time a group of injections are to be made, another disposable injection transmitter 10 is stuck in the primary injection site 76 and the process is repeated.

The peripheral side wall of the auxiliary injection site 18 is long enough (about ¼ inch or more) to be gripped between the thumb and a finger so that it can be carefully introduced into a primary injection site straight and without coring and without hitting the side of that injection site. As mentioned, the radial wall 26 also helps the ring 56 in the auxiliary injection site 18 identify the target spot for the point of an injection needle.

Once the injection needle enters the passage 40 or 40' through the body 14, the passage, and the auxiliary needle 16 serve as guides to the direction of the injecting needle so that it is kept straight. The auxiliary needle is fairly large, which allows most injecting needles to enter it. The passage 40 or 40' through the body may be straight as in FIG. 4 (and coaxial with the auxiliary needle passage) or it may diverge, as in FIG. 3, to facilitate the reception of various sizes of injecting needles.

Since the disposable injection transmitter 10 is so inexpensive, the cost of its use is nominal. However, the savings from elimination of wasted fluid bags 66 is substantial. Furthermore, contamination of the patient such as occurs upon leakage of a primary injection site 76 is eliminated. Finally, the life of an infuse-aid implant is extended greatly because, instead of a group of injections, a single injection is made by the needle 16 of the disposable injection transmitter 10.

There are various changes and modifications which may be made to this invention as would be apparent to those skilled in the art. However, any of these changes or modifications are included in the teaching of this disclosure and this invention is limited only by the scope of the claims appended hereto.

What is claimed is:

1. A disposable injection transmitter for substantially reducing the number of punctures of the membrane of a primary injection site by receiving multiple needle punctures for fluid injections while introducing a single needle puncture of the primary injection site membrane comprising a body having a fluid passage through it, a hollow auxiliary needle connected to the body at one end of and in communication with the fluid passage, an elastomeric wall permanently connected to the body and positioned to close the other end of the passage, the wall completely closing the body except for the communication with the fluid passage through the auxiliary needle, the wall adapted to receive fluid injecting syringe needles successively through it while the wall remains connected to the body, the wall having a face generally normal to the fluid passage so that an injection needle stuck through the wall will enter the fluid passage.

2. The disposable injection transmitter of claim 1 wherein the elastomeric wall is latex.

3. The disposable injection transmitter of claim 1 wherein the elastomeric wall is at least two millimeters thick.

4. The disposable injection transmitter of claim 1 wherein the passage through the head is tapered from a larger diameter at the open end to a smaller diameter at the end in communication with the needle passage.

5. The disposable injection transmitter of claim 4 wherein the smaller diameter of the head passage is about equal to the diameter of the needle passage.

6. The disposable injection transmitter of claim 1 wherein the head passage is no more than about three-fourths inch long.

7. The disposable injection transmitter of claim 1 wherein the face of the wall has a ring formed in it to identify where an injection needle should be started to penetrate the wall.

8. The disposable injection transmitter of claim 1 wherein the elastomeric wall is a solid member having a peripheral side normal to the face, the peripheral side extending at least one-fourth inch from the face.

9. The disposable injection transmitter of claim 1 including an annular shoulder formed on the body adjacent said other end, the elastomeric wall having an annular skirt for wrapping about the annular shoulder.

10. A disposable injection transmitter for penetrating only once an existing primary injection site and receiving a plurality of injections and transmitting fluid therefrom through and beyond the primary injection site for thereby substantially reducing the number of punctures of the membrane of the primary injection site comprising a body having a leading end and a trailing end, a fluid passage through the body between the leading end and the trailing end, an auxiliary needle joined to the leading end of the body, a passage through the auxiliary needle in communication with the body passage, an auxiliary injection site permanently joined to the trailing end of the body extending across and closing the trailing end of the body passage, the auxiliary injection site comprising a wall of elastomeric material for being penetrated successively by syringe needles while the auxiliary injection site remains joined to the body, and means to seal the wall and the body against the passage of air therebetween, the body being completely closed except for communication with the passage through the needle.

11. The disposable injection transmitter of claim 10 wherein the body passage is at right angles to the membrane and in the path of the discharge end of a fluid injection needle.

12. The disposable injection transmitter of claim 10 including a sheath having a cavity for receiving and covering the auxiliary needle.

13. The disposable injection transmitter of claim 10 wherein the means to seal comprises an annular rim extending laterally outwardly of the body, a cylindrical resilient skirt contiguous with the wall extending across the rim, the trailing end of the body opening being within the annular rim.

14. The disposable injection transmitter of claim 13 wherein the body includes an annular side wall and the rim is between the trailing end of the body and the annular side wall and projects laterally outwardly of the annular side wall.

15. The disposable injection transmitter of claim 10 wherein the body passage has a diameter slightly larger than the diameter of needles stuck through the auxiliary needle.

16. The disposable injection transmitter of claim 10 wherein the body has a wall extending radially beyond the auxiliary injection site against which manual pressure can be exerted to press the auxiliary needle through a primary injection site and to facilitate withdrawal thereof.

* * * * *